United States Patent [19]

Larock et al.

[11] Patent Number: 4,650,881
[45] Date of Patent: Mar. 17, 1987

[54] SYNTHESIS OF ISOCOUMARINS VIA THALLATION-OLEFINATION OF ARENES

[75] Inventors: Richard C. Larock, Ames, Iowa; Sudarsanan Varaprath, Midland, Mich.

[73] Assignee: Iowa State University Research Foundation, Inc., Ames, Iowa

[21] Appl. No.: 718,649

[22] Filed: Apr. 1, 1985

[51] Int. Cl.$^4$ .......................................... C07D 311/76
[52] U.S. Cl. ................................... 549/290; 549/283; 549/265; 549/280; 549/289; 549/269; 549/312; 549/304; 549/305
[58] Field of Search ................................ 549/283, 290

[56] References Cited

U.S. PATENT DOCUMENTS

| | | | |
|---|---|---|---|
| 2,615,024 | 10/1952 | Clinton et al. | 549/283 |
| 3,585,214 | 6/1971 | Boschetti et al. | 549/289 |
| 3,636,004 | 1/1972 | Bode et al. | 549/283 |
| 3,784,600 | 1/1974 | von Strandtmann et al. | 549/289 |
| 3,803,175 | 4/1974 | Sparks et al. | 549/283 |
| 3,808,232 | 4/1974 | Hardt et al. | 549/283 |
| 4,083,857 | 4/1978 | Townend et al. | 549/283 |
| 4,162,326 | 7/1979 | Milhailovski | 549/289 |
| 4,235,781 | 11/1980 | Kaufman | 549/289 |
| 4,279,823 | 7/1981 | Larock | 549/280 |
| 4,296,039 | 10/1981 | Della Valle | 549/289 |
| 4,312,883 | 1/1982 | Baccichetti et al. | 549/289 |

OTHER PUBLICATIONS

Larock et al., Chem. Abst. 101: 110682k.

*Primary Examiner*—Jane T. Fan
*Attorney, Agent, or Firm*—Zarley, McKee, Thomte, Voorhees & Seas

[57] ABSTRACT

Arenes, such as benzoic acid and substituted benzoic acids, are readily thallated by thallium(III) compounds such as the trifluoroacetate and subsequently reacted with palladium chloride and simple olefins, dienes, allylic halides, vinyl halides, vinyl esters, or unsaturated cyclopropanes or unsaturated cyclobutanes to give isocoumarins.

14 Claims, No Drawings

SYNTHESIS OF ISOCOUMARINS VIA THALLATION-OLEFINATION OF ARENES

GRANT REFERENCE

The invention described herein was made in part in the course or work under a grant from the National Institutes of Health No. GM 24254.

BACKGROUND OF THE INVENTION

Isocoumarins, and 3,4-dihydroisocoumarins are known biologically active compounds. Isocoumarins contain the basic ring system:

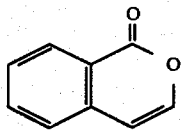

Some substituted isocoumarins are effective as local anesthetics. Other coumarin and isocoumarin derivatives have been reported as having strong hypotensive activity, spasmolytic activity on the sphincter of Oddi and choleretic activity. Still other 4-substituted coumarins for example have been reported as useful as gastric antisecretory agents, with still other coumarin and substituted coumarin compounds being useful as odiferous agents for use in cosmetic preparation, and others as useful intermediates in the preparation of certain known biologically active chromones, as well as certain 7-hydroxycoumarins having known activity as coronary vasodilating activity. It can be seen, therefore, because of the wide range of uses including uses as varied as cosmetic odiferous agents to biologically active compounds for a variety of different pharmacological uses, there is a continuing need for a convenient and efficient synthesis of isocoumarin ring containing compounds, a need which is of contemporary and practical importance.

It is a primary object of the present invention to provide an improved one pot process for preparation of isocoumarin ring containing compounds and 3,5-dihydroisocoumarins from simple benzoic acids.

It is a further object of the present invention to provide isocoumarin ring containing compounds and 3,4-dihydroisocoumarins from simple olefins, dienes, allylic halides, vinyl halides, vinyl esters, and unsaturated cyclopropanes and cyclobutanes by reacting an arene with an electrophilic thallium salt to provide an aryl thallium intermediate compound which is in turn reacted with the olefins, dienes, allylic halides, vinyl halides, vinyl esters, unsaturated cyclopropane or cyclobutane to provide an isocoumarin or a 3,4-dihydroisocoumarin.

It is an additional object of the present invention to avoid the disadvantages of the prior art processes involving complex multi-stage, and step, reactions to prepare isocoumarins from simple benzoic acids.

A still further objective of the present invention is to provide a practical single pot synthesis of isocoumarins and 3,4-dihydroisocoumarins in high yields suitable for commercial use.

The method and manner of accomplishing each of the above objectives as well as others will become apparent from the detailed description which follows.

SUMMARY OF THE INVENTION

This invention relates to a process of preparing isocoumarin and 3,4-dihydroisocoumarin ring containing compounds. In the process an arene, preferably benzoic acid or a substituted benzoic acid, is reacted with an electrophilic thallium salt, preferably thallium-(III) trifluoroacetate, in the presence of an organic solvent to provide an aryl thallium intermediate compound. The aryl thallium intermediate compound is reacted in situ with an unsaturated organic compound such as a simple olefin, a diene, an allylic halide, a vinyl halide, a vinyl ester, an unsaturated cyclopropane or cyclobutane, in the presence of a palladium halide salt to yield the desired isocoumarin or 3,4-dihydroisocoumarin.

DETAILED DESCRIPTION OF THE INVENTION

While the reaction of this invention has as one of its primary advantages the fact that it is a single pot reaction, for purposes of discussion it may be conveniently broken into two steps. In the first step an arene is reacted with an electrophilic thallium salt. The reaction may be represented with benzoic acid by the following equation:

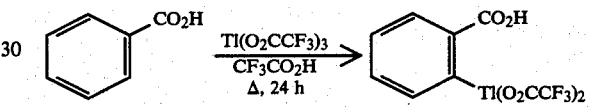

It can be seen that in the reaction of the equation represented above, benzoic acid is thallated by thallium(III) trifluoroacetate to provide a thallated intermediate compound which can be described as an ortho-thallated benzoic acid. In accordance with the first step, an arene, such as benzoic acid as shown above, is reacted with an electrophilic thallium salt in the presence of an organic solvent to provide thallation of the arene to give an arylthallium intermediate compound.

Of course, the precise arene used in this initial thallation reaction is not critical. Generally, the most satisfactory results are achieved when the arene compound is a $C_{12}$ or less structure and most preferably a $C_6$ to $C_{12}$ structure. Most preferably the arene is a benzoic acid or a substituted benzoic acid. Substituents which may be substituted on the aromatic ring without effecting the reaction are halide, $C_1$ to $C_{12}$ alkyl, $C_1$ to $C_{12}$ alkoxy, nitro, amido, or the phenolic group. Preferably the arene is benzoic acid, substituted with either a halide, methoxy or alkyl group.

The electrophilic thallium salt employed is not critical the essential factor simply being that the anion must be one which tends to make the thallium ion sufficiently reactive with respect to the substituents on the aromatic ring. Suitable anions have been found to be trifluoroacetate, perchlorate, nitrate and acetate. Because of the ease of formation and availability, it is preferred that the electrophilic thallium compound be thallium trifluoroacetate. For details with respect to preparation of thallium trifluoroacetate, see McKillop, et al. *J. Am. Chem. Soc.*, Vol. 93, p. 4841–4844 (1971) and Taylor, et al. *J. Am. Chem. Soc.*, Vol. 93, p. 4845 et seq. (1971) which are incorporated herein by reference. The solvent employed in this first reaction step is not critical, and generally may be any solvent which will suitably dissolve the thallium compound and the starting aromatic compound. Suitable solvents are preferably polar solvents such as trifluoroacetic acid, tetrahydrofuran, and acetic acid, or less polar solvents such as ether, methylene chloride and chloroform. Of course, others such as acetonitrile may also be employed conveniently.

The reaction temperature and pressure are not critical factors. Generally, the reaction may be run at any temperature from −20° C. up to 100° C., with the temperature of refluxing trifluoroacetic acid ($\approx 72°$ C.) being satisfactory. The reaction time varies depending upon the reactivity of the starting aromatic compound and can be from a mere few minutes, up to as long as 96 hours. Commonly, a 24–48 hour thallation reaction time is sufficient.

After the initial formation of the aryl thallium intermediate compound, if desired, the salt may be isolated by removing the solvent under vacuum and recrystallizing. It is, however, not necessary to even isolate the intermediate unless one has a specific desire to do so. If isolation of the intermediate is not deemed important the reaction can directly proceed to its second phase which involves removing the original solvent (usually trifluoroacetic acid) and reacting the aryl thallium intermediate compound with an unsaturated organic compound selected from the group consisting of simple olefins, dienes, allylic halides, vinyl halides, vinyl esters, unsaturated cyclopropanes and cyclobutanes, with the reaction occurring in the presence of a palladium halide salt.

The second phase reaction for alkenes may be represented by the following equation showing reaction of the intermediate thallium compound (formed by reaction of benzoic acid with thallium trifluoroacetate) with 3,3-dimethyl-1-butene, in the presence of palladium chloride.

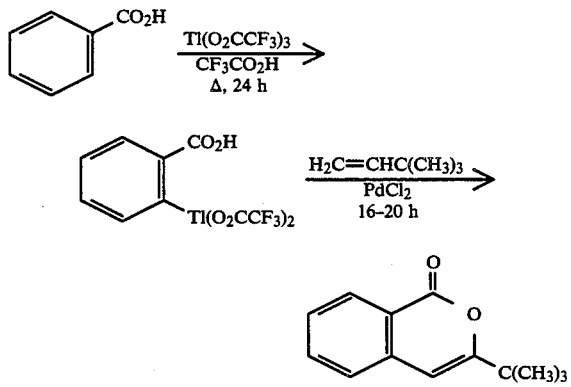

It can be seen that the reaction yields 3-tert-butylisocoumarin. Investigation of this reaction with various solvents revealed that the preferred solvents are acetonitrile and methylene chloride. With regard to the olefin reaction, it is preferred that the olefin be a $C_2$ to $C_{12}$ monosubstituted terminal olefin or a di-substituted internal olefin of $C_4$ to $C_{12}$ chain length. Generally it can be said that the more highly substituted the double bond, the less reactive it will be. It is therefore preferred that the olefin be as little substituted as possible. Substituents which may replace hydrogen on the olefin with satisfactory results being obtained are primary, secondary and tertiary alkyl, phenyl, carbomethoxy, and cyano. As shown in Table I, entries 6 and 7, when the olefin is substituted with an ester or cyano group, the major product is the phthallide ring system. Table I below illustrates generally the preparation of isocoumarins using simple alkenes. In Table I, R and $R_1$ can be hydrogen, alkyl, aryl or arylalkyl groups.

The preferred amount of olefin reagent is two equivalents. The addition of 2 equivalents of $Et_3N$, as well as an inorganic base such as $Na_2CO_3$ (2 equiv.) was found to give a cleaner reaction and by refluxing (80° C.) the reaction time for cyclization could be reduced to 5 h.

It can be seen from the above reaction that it is essential that the reaction be conducted in the presence of a palladium halide salt, preferably palladium chloride. While not important for describing the overall process, the believed reason for the essential nature of the palladium salt is that the palladium salt is necessary for the cyclization to form the isocoumarin. The scheme by which it is believed this occurs is disclosed in a paper on this same topic, Larock, et al. *J. Am. Chem. Soc.*, 1984, 106, 5274 at p. 5275, which is incorporated herein by reference. Basically during the process, the palladium(II) is reduced to palladium(O), but the thallium(III) salt formed in the initial transmetalation step apparently reoxidizes the palladium(O) to palladium(II), which then promotes intramolecular (acyloxy) palladation of the styrene intermediate. A second palladium hydride elimination affords the isocoumarin. At this stage, the palladium has once again been reduced to palladium(O) and all of the reoxidant has also been used up. The overall reaction therefore requires one palladium molecule per arene molecule.

The amount of palladium salt employed is generally an equimolar amount with the amount of thallated arene employed.

In addition to reaction with simple alkenes, the thallated arene may also be reacted with acyclic or cyclic 1,2- or 1,3-dienes, or in addition acyclic 1,4-dienes. It is preferred that the diene be a 1,2- or 1,3-diene of $C_3$ to $C_{12}$ chain length. Generally the less substituted the double bonds the more reactive. Thus it is preferred that the least amount of substitution on the double bond carbons occur. The procedure employed with the 1,2-, 1,3- and 1,4-dienes is identical with the procedure for the simple olefins. Table II shown below shows reactions of 1,2-, 1,3- and 1,4-dienes in the process of this invention to yield 3,4-dihydroisocoumarins. The reaction may also be run under conditions generally identical to those of simple alkenes.

However, it was discovered that the addition of LiCl (2 equiv.) and the omission of the bases resulted in comparable or better yields of isocoumarin product. The reaction with allylic halides is catalytic and is represented by the following equation:

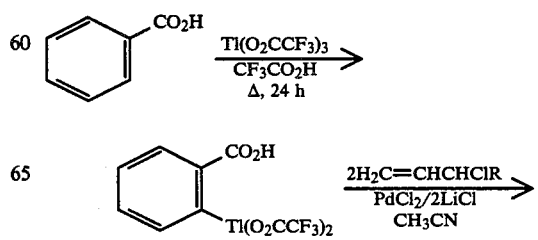

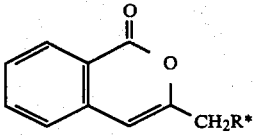

*R can be hydrogen alkyl, aryl or arylalkyl of $C_1$ to $C_{12}$.

It has been found that where one employs organic halides such as allylic halides, the amount of palladium chloride required is not equimolar, but is catalytic. In this case the yields of the isocoumarins are satisfactory with only 10% palladium chloride used as compared with other examples where equimolar amounts were employed. The reaction apparently proceeds by palladium promoted allylation of the arene and subsequent palladium(II)-promoted cyclization of the resulting ortho-allylic benzoic acids. In the allylation step, the palladium(II) species is not reduced so that the reaction becomes catalytic with respect to palladium. The thallium(III) remains available for oxidation of the palladium(O) produced in the final palladium hydride elimination. Examples 25 and 26 below illustrate the reaction with allylic chlorides.

Vinyl halides and vinyl esters, particularly vinyl acetates will proceed with the same general reaction as that shown for alkenes. The y yield 4-substituted isocoumarins. It is preferred that the vinyl halide be bromide or iodide, and that they be acyclic compounds of $C_2$ to $C_{12}$ carbon chain length. Table III below showing examples 27-34 are examples of vinyl halides and acetates to yield isocoumarins. It is important to note that this reaction is catalytic in palladium chloride.

The reaction also proceeds satisfactorily where the compound reacted is a vinyl cyclopropane or a vinyl cyclobutane. This can be illustrated for vinyl cyclopropane with the following equation, where $R_1$, $R_2$ and $R_3$ represent hydrogen or $C_1$ to $C_{12}$ substituents.

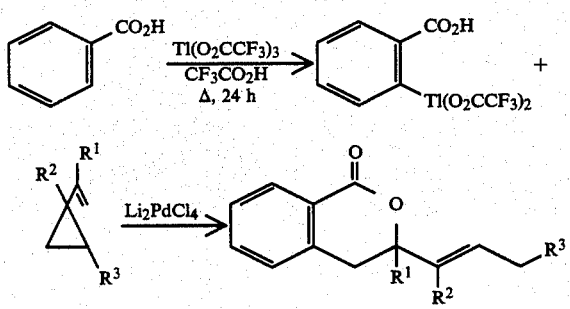

These are illustrated in the examples 35-39 of Table IV shown below.

In summary, it can be seen that a highly efficient process of thallation and subsequent palladium promoted olefination of benzoic acids and substituted benzoic acids is provided to give a convenient route to the biologically important isocoumarin and 3,4-dihydroisocoumarin rings. The sequence requires only inexpensive, readily available starting materials and is flexible enough to afford a variety of substitution patterns. The fact that the reaction can be made catalytic with respect to palladium makes this approach an especially attractive one. Preliminary studies also would seem to indicate that the thallation-olefination process can be successfully employed on a variety of other aromatic substrates to provide a novel new approach to a number of other important heterocyclic ring systems other than the isocoumarins and 3,4-dihydroisocoumarins.

The following examples are offered to further illustrate but not limit the process of the present invention.

In each of the examples, the following general procedure was employed for the thallation of the benzoic acids. Since the number of examples is so voluminous it will, for efficiency purpose, serve to show the general procedure for the thallation of benzoic acids with the understanding that an identical or similar procedure was employed with each of the unsaturated compounds prepared in accordance with the tables shown.

GENERAL PROCEDURE

Thallium(III) trifluoroacetate (11.3 g, 0.02 mol) was dissolved in argon-saturated trifluoroacetic acid (40 mL). Benzoic acid (2.5 g, 0.02 mol) was added, and the contents were stirred and gently refluxed in an 80° C. oil bath for 24 h. The flask was cooled to room temperature, and the white crystals that precipitated were collected by filtration and washed with cold, dry methylene chloride. The yield of the ortho-thallated benzoic acid ranges from 90% to 95%.

m-Methoxybenzoic acid was thallated as described above with the following modifications: The mixture was heated at reflux temperature for a shorter reaction time (14 h). The crystals that settled on cooling were collected by quick filtration into a round-bottom flask and dried by using a vacuum pump. The off-white solid was not washed with methylene chloride because of its solubility in this solvent.

m-Chlorobenzoic acid and m-methylbenzoic acid were thallated as described for m-methoxybenzoic acid (thallation times 40 and 96 h, respectively).

REACTION OF THALLATED BENZOIC ACIDS WITH SIMPLE OLEFINS

The thallated benzoic acid (5 mmol) and palladium-(II) chloride (5 mmol) were weighed into a round-bottom flask. For reactions with certain olefins, lithium chloride (10 mmol) was also added to the reaction flask. The solvent (10 mL) was added followed by addition of the appropriate olefin (10 mmol). The contents were stirred at room temperature for 20 h. Triethylamine (10 mmol) and anhydrous sodium carbonate (10 mmol) were then added in that order. The contents were gently heated at reflux temperature for 5 h. After cooling to room temperature, ether (20 mL) was added and the solution was filtered through diatomaceous earth (Celite). The residue was washed with ether (100 mL). The combined ether solutions were washed twice with 15 mL of saturated ammonium chloride solution, dried over anhydrous MgSO₄, and concentrated to an oil using a rotary evaporator. The crude products were purified by distillation, recrystallization, or flash chromatographic separation on silica gel using a hexane/ethyl acetate solvent mixture as eluant. The following described compounds were prepared by using this basic procedure.

The following procedure illustrating synthesis of isocoumarin (see Table I, example 1 below) is illustrative. Ortho-thallated benzoic acid as illustrated in the first equation of this specification, (0.28 g, 0.5 mmol) was reacted with PdCl₂ (89 mg, 0.5 mmol) and excess ethylene (a balloon full) in acetonitrile as the solvent followed by treatment with triethylamine (0.14 mL, 1.0 mmol) and anhydrous sodium carbonate (106 mg, 1.0 mmol) as described above. This gave a crude mixture containing several products. Isocoumarin was separated by flash chromatography on silica gel using hexane/ethyl acetate (19:1) as the eluant. It was further purified by recrystallization from hexane to obtain the pure product: yield 54 mg, 37%; mp 46°–47° C. (lit. mp 47° C.); $^1$H NMR (CDCl$_3$) δ6.3 (d, 1H, C$_4$-H,J=6 Hz), 7.2 (d, 1H, C$_3$-H,J=6 Hz), 7.2–8.25 (m, 4H, Ar-H); IR (CCl$_4$) 1750, 1730 (C=O), 1700 (C=C) cm$^{-1}$.

In every instance the reaction products were confirmed by instrumental analysis techniques.

It is believed that the tables shown below are sufficient for illustrating the remaining examples without duplicating what is essentially the same procedure as illustrated above in the general procedure. However, for sake of completeness, the applicants incorporate by reference pages 5280–5283, J. Am. Chem. Soc., Vol. 6, No. 18, 1984 which illustrate the procedure previously outlined herein.

Table I illustrates olefination of thallated benzoic acids using simple alkenes.

TABLE I

Olefination of Thallated Benzoic Acids Using Simple Alkenes

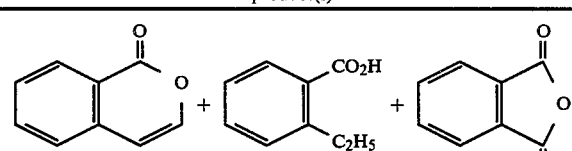

| entry | olefin | X | product(s) | isolated yield, %$^a$ |
|---|---|---|---|---|
| 1 | H$_2$C=CH$_2$ | H | 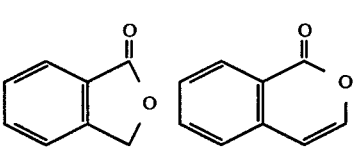  5:5:1 | 80$^b$ |
| 2 | H$_2$C=CH$_2$ | H | 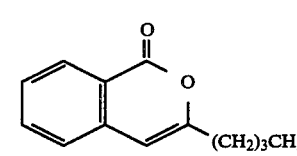  92:8 | 60$^c$ |
| 3 | H$_2$C=CH(CH$_2$)$_3$CH$_3$ | H | 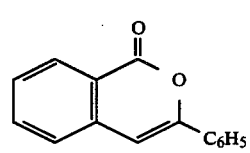 | 40 |
| 4 | H$_2$C=CHC$_6$H$_5$ | H | 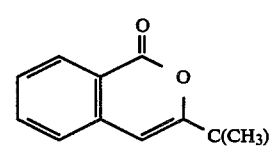 | 79 |
| 5 | H$_2$C=CHC(CH$_3$)$_3$ | H | 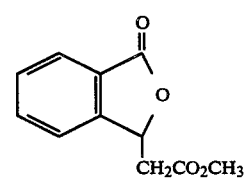 | 73 |
| 6 | H$_2$C=CHCO$_2$CH$_3$ | H |  | 56$^d$ |

TABLE I-continued
Olefination of Thallated Benzoic Acids Using Simple Alkenes

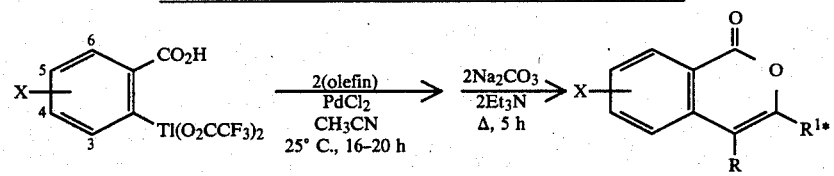

| entry | olefin | X | product(s) | isolated yield, %[a] |
|---|---|---|---|---|
| 7 | $H_2C=CHCN$ | H | [isochromanone with CH₂CN substituent] | 55[d] |
| 8 | cis-$CH_3CH=CHCH_3$ | H | [two isocoumarin products with CH₃ and CH₂CH₃ substituents] 3:1 | (73)[e] |
| 9 | [cyclohexene] | H | [two cyclohexenyl-fused products] 5:1 | (61)[e] |
| 10 | $H_2C=CHC(CH_3)_3$ | 5-Cl | [two chloro-substituted isocoumarin products with C(CH₃)₃] 9:1 | (65)[e] |
| 11 | $H_2C=CHC(CH_3)_3$ | 5-$CH_3$ | [two methyl-substituted isocoumarin products with C(CH₃)₃] 6:1 | (50)[e] 41 |
| 12 | $H_2C=CHC(CH_3)_3$ | 3-$OCH_3$ | [two methoxy-substituted isocoumarin products with C(CH₃)₃] 10:1 | 66[e] |

[a] Yields determined by gas chromatography are in parentheses.
[b] 10 equiv of LiCl were added to the reaction.
[c] DMF was used as the solvent.
[d] This reaction was run with 10% PdCl₂ for 2 days at room temperature and then 2 equiv of Et₃N were added and refluxed for 20 h.
[e] The reaction was run at room temperature for 2 days with 2 equiv of LiCl added (no bases added).
\*R and R[1] can be hydrogen, alkyl or aryl groups.

Reaction of 1,2-, 1,3- and 1,4-dienes is illustrated by examples 13–23 shown in Table II below.
TABLE II
Olefination Using Dienes
| entry | diene | product(s) | isolated yield, % |
|---|---|---|---|
| 13 | $H_2C=CHCH=CH_2$ | 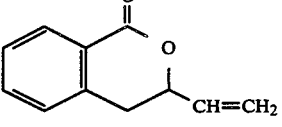 | 87 |
| 14 | trans-$H_2C=CHCH=CHCH_3$ | 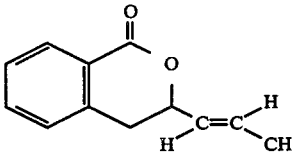 | 71 |
| 15 | cis-$H_2C=CHCH=CHCH_3$ | | 78 |
| 16 | $H_2C=CHC(CH_3)=CH_2$ | 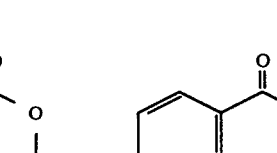 9:4 | 70 |
| 17 | 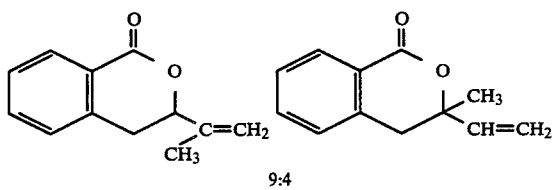 |  | 45 |
| 18 | $H_2C=C=CHCH_3$ | 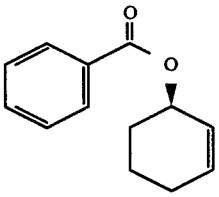 | 39 |
| 19 | $H_2C=C=CHC_6H_5$ | 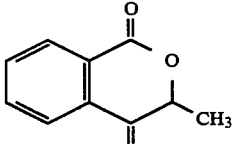 5:1:1 | 54 |
| 20 | $H_2C=C=C(CH_3)_2$ | 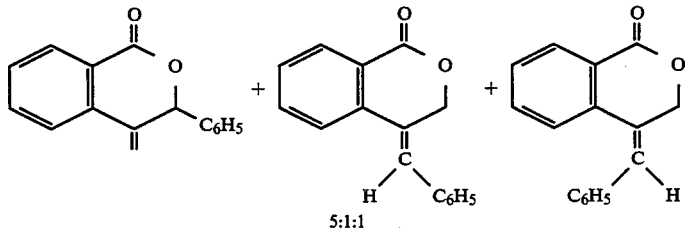 | 67 |
| 21 | 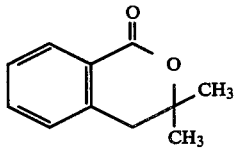 |  | 70 |

TABLE II-continued
Olefination Using Dienes

| entry | diene | product(s) | isolated yield, % |
|---|---|---|---|
| 22 | [cyclononene structure] | [isocoumarin fused bicyclic product] | 56 |
| 23 | H₂C=CHCH₂CH=CH₂ | [isocoumarin with vinyl side chain product] | 34 |

Examples 25 and 26 illustrate the preparation of isocoumarins from allylic halides in accordance with the equation presented earlier.

EXAMPLE 25

Reaction with Allylic Chlorides: 3-Methylisocoumarin. Catalytic PdCl$_2$: palladium chloride (0.09 g, 0.5 mmol), LiCl (0.04 g, 1 mmol), and allyl chloride (0.77 g, 10 mmol) were added to the thallated benzoic acid (5 mmol) [prepared from 0.61 g (5 mmol) of benzoic acid and 1.37 g (5 mmol) of thallium trifluoroacetate] in acetonitrile as solvent. After it was stirred at room temperature for 2 days, the reaction was worked up by the standard isolation procedure. The crude product was recrystallized from hexane to obtain 48% of the pure product; mp 71° C. (lit. mp 73°–74° C.); $^1$H NMR (CCl$_4$) δ2.2 (s, 3H, CH$_3$), 6.1 (s, 1H, C$_4$H), 7.25–7.6 (m, 3H, ArH), 8.0–8.2 (m, 1H, C$_8$H); IR (CCl$_4$) 1740 (C=O), 1670 (C=C) cm$^{-1}$. Stoichiometric PdCl$_2$: This was carried out in a manner identical with the catalytic procedure, except that an equivalent amount of palladium chloride (with respect to the thallated benzoic acid) was employed. By use of the standard isolation procedure, the product yield was estimated to be 59% by using gas chromatography with tetradecane as the internal standard.

EXAMPLE 26

3-Ethylisocoumarin. The general thallation described above was followed using 3-chloro-1-butene as the allylic halide and 10 mol % of PdCl$_2$. After routine isolation, the pure product was obtained by recrystallization from hexane; mp 69° C.; $^1$H NMR (CCl$_4$) δ1.3 (t, 3H, CH$_3$, J=7 Hz), 2.55 (q, 2H, CH$_2$, J=7 Hz), 6.15 (s, 1H, C$_4$H), 7.15–7.7 (m, 3H, ArH), 8.0–8.2 (m, 1H, C$_8$H); IR (CCl$_4$) 1735 (C=O), 1650 (C=C) cm$^{-1}$; mass spectrum, m,/e 174.067 40 (calcd for C$_{11}$H$_{10}$O$_2$, 174.068 08).

The reaction of vinyl halides, particularly bromides and iodides and vinyl acetate as representative of vinyl esters are illustrated in Table III below with examples 27–34.

TABLE III
Olefination Using Vinyl Halides or Acetates

| entry | vinyl halide or acetate | product(s) | | isolated Yield, % |
|---|---|---|---|---|
| 27 | H₂C=CHBr | [isocoumarin] | | 71 |
| 28 | cis-CH₃CH=CHBr | [3-methylisocoumarin isomers] 9:2 | | 69 |
| 29 | cis-n-C$_4$H$_9$CH=CHBr | [hexahydro isocoumarin with C$_4$H$_9$ isomers] | 6:1 | 32, 35$^a$ |
| 30 | trans-n-C$_4$H$_9$CH=CHBr | | 4:1 | 41, 58$^a$ |

TABLE III-continued
Olefination Using Vinyl Halides or Acetates

| entry | vinyl halide or acetate | product(s) | isolated Yield, % |
|---|---|---|---|
| 31 | cis-C$_4$H$_9$CH=CHI | 10:1 | 35, 45[a] |
| 32 | C$_6$H$_5$CBr=CH$_2$ | 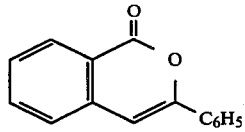 | 31 |
| 33 | H$_2$C=CHOAc | 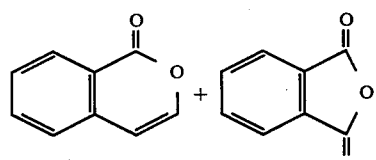 2:1 | 68 |
| 34 | H$_2$C=C(OAc)CH$_3$ | 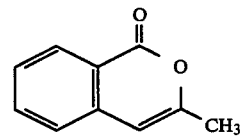 | 39 |

[a] Reaction was refluxed 20 h.

Reaction of vinyl cyclopropanes as illustrative of both vinyl cyclopropanes and vinyl cyclobutanes is represented by Table IV.

TABLE IV
Olefination Using Vinylcyclopropanes

| entry | vinylcyclopropane | product(s) | isolated yield, % |
|---|---|---|---|
| 35 |  | 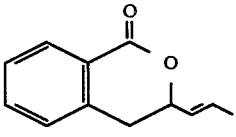 | 64 |
| 36 |  | 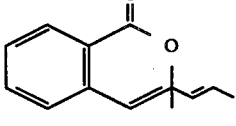 | 40(50) |
| 37 |  | 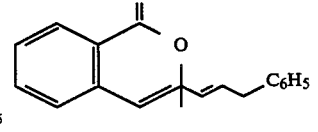 | 32(42) |
| 38 |  | " | 26 |
| 39 |  | 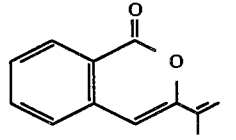 | (65) |

What is claimed is:

1. A process of preparing isocoumarin and 3,4-dihydroisocoumarin ring compounds, comprising:
   reacting an arene selected from the group consisting of benzoic acid and substituted benzoic acid substituted on the aromatic ring with a moiety selected from the group consisting of halide, C$_1$ to C$_{12}$ alkyl, C$_1$ to C$_{12}$ alkoxy, nitro, amido, and phenolic, with an electrophilic thallium salt in the presence of an organic solvent to provide an arylthallium intermediate compound; and
   reacting said arylthallium intermediate compound with an unsaturated organic compound selected from the group consisting of olefins consisting of C$_2$ to C$_{12}$ terminal olefins and internal olefins of C$_4$ to C$_{12}$ chain length, 1.2 and 1.3 dienes, allylic halides, vinylic halides, vinylic acetates, vinylic cyclopropanes and vinylic cyclobutanes,
   said reaction occurring in the presence of a palladium salt,
   to yield an isocoumarin or a 3,4-dihydroisocoumarin.
2. The process of claim 1 wherein the palladium salt is a palladium halide salt.
3. The process of claim 1 wherein said palladium salt is palladium chloride.
4. The process of claim 1 wherein said unsaturated compound is an alkene.
5. The process of claim 1 wherein said unsaturated compound is selected from the group of vinylic cyclopropanes and vinylic cyclobutanes.
6. The process of claim 1 wherein said unsaturated compound is an allylic halide.
7. The process of claim 1 wherein said unsaturated compound is a vinyl halide.
8. The process of claim 1 wherein said organic solvent is selected from the group of CH$_3$CN and CH$_2$Cl$_2$.
9. The process of claim 1 wherein the amount of palladium salt is a catalytically effective amount.
10. The process of claim 1 wherein the reaction is conducted under refluxing conditions for from 2 to 24 hours.

11. The process of claim 1 wherein the refluxed product is thereafter cooled to room temperature to allow crystallization.

12. The process of claim 1 wherein an additional step, subsequent to the reaction with that unsaturated compound includes adding a base selected from the group consisting of triethylamine and sodium carbonate and refluxing.

13. The process of claim 12 wherein said refluxing is at a temperature of about 80° C. for about 5 to 24 hours.

14. The process of claim 1 wherein lithium chloride is added in conjunction with the palladium halide salt.

* * * * *